United States Patent [19]

Denis et al.

[11] Patent Number: 4,954,273
[45] Date of Patent: * Sep. 4, 1990

[54] OIL FORMULATIONS CONTAINING OVERBASED MULTI-FUNCTIONAL ADDITIVE

[75] Inventors: Richard A. Denis, Auburn Township, Cuyahoga County; Frederick W. Koch, Willoughby Hills, both of Ohio

[73] Assignee: The Lubrizol Corporation, Wickliffe, Ohio

[*] Notice: The portion of the term of this patent subsequent to Nov. 15, 2005 has been disclaimed.

[21] Appl. No.: 263,578

[22] Filed: Oct. 27, 1988

Related U.S. Application Data

[63] Continuation-in-part of Ser. No. 20,287, Feb. 27, 1987, Pat. No. 4,784,781.

[51] Int. Cl.$^5$ .................................. C10M 105/22
[52] U.S. Cl. ........................................ 252/39; 252/38; 252/40; 252/41; 252/56 R
[58] Field of Search ............... 252/38, 39, 56 R, 40, 252/41

[56] References Cited

U.S. PATENT DOCUMENTS

| | | | |
|---|---|---|---|
| 2,801,972 | 8/1957 | Bartlett | 252/41 |
| 3,625,893 | 12/1971 | Brook et al. | 252/32.7 |
| 3,791,971 | 2/1974 | Lowe | 252/33.4 |
| 3,828,086 | 8/1974 | Kennedy | 252/39 |
| 3,856,688 | 12/1974 | Kennedy | 252/39 |
| 4,088,590 | 5/1978 | Knoblauch et al. | 252/73 |
| 4,265,774 | 5/1981 | Langdon | 252/49.3 |
| 4,579,672 | 4/1986 | Brecker | 252/49.8 |
| 4,784,781 | 11/1988 | Denis | 252/39 |

FOREIGN PATENT DOCUMENTS 0018681 11/1980 European Pat. Off. .
0039111 11/1981 European Pat. Off. .
2088863 6/1982 United Kingdom .
2152050 7/1985 United Kingdom .

*Primary Examiner*—Olik Chaudhuri
*Assistant Examiner*—James M. Hunter, Jr.
*Attorney, Agent, or Firm*—Forrest L. Collins; Frederick D. Hunter; Robert A. Franks

[57] ABSTRACT

Oil based compositions including crank case oils and in particular diesel engine crank case oils are disclosed which are comprised of oil having a multi-functional additive component therein. The additive component is present in sufficient amounts so as to provide improved performance characteristics to the composition such as pH stability, water tolerance and antiwear characteristics. The additive is an overbased salt of a compound represented by the general structural formula (I):

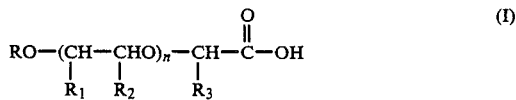

wherein R is a hydrocarbyl, preferably iso-stearyl, $R_1$, $R_2$, and $R_3$ are independently hydrogen or aklyl, preferably hydrogen and n is 1 to 20, preferably 1 to 5. Statistical mixtures and mixed salts of the additive compound are also disclosed as are fully formulated oils. The additive is an effective pH stabilizer, EP agent, and water tolerance fix in a variety of functional fluids and lubricating compositions such as crank case oils, particularly diesel engine crank case oils. In crank case oil compositions the additive provides a number of improved performance properties, most importantly improved detergent capabilities (resulting in cleaner engine parts) and improved frictional properties (resulting in improved fuel efficiency).

20 Claims, No Drawings

OIL FORMULATIONS CONTAINING OVERBASED MULTI-FUNCTIONAL ADDITIVE

CROSS REFERENCES

This is a continuation-in-part of U.S. application Ser. No. 07/020/287 filed Feb. 27, 1987 now U.S. Pat. No. 4,784,781 which is incorporated herein by reference and to which priority is claimed under 35 USC Section 120.

FIELD OF THE INVENTION

The invention relates to the field of oil formulations containing an overbased multifunctional detergent additive which improves the water tolerance and other characteristics of the formulation without impacting adversely on other properties such as extreme pressure/anti-wear properties. More specifically the invention relates to crank case oil formulations having therein overbased salts of iso-stearylpentaethylene glycolacetic acid which provide improved high temperature performance regarding detergency.

BACKGROUND OF THE INVENTION

Oil lubricating formulations such as crank case oils are easily contaminated with water and acids created during combustion. Accordingly water compatibility and pH stability are important properties. In addition, improved detergent capabilities and the reduction of friction. The significance of these properties is most important under severe conditions such as when lubricants come into contact with water under the extreme pressure and temperature conditions during combustion.

In connection with crank case oils, it is particularly important to maintain engine cleanliness and frictional resistance in order to keep engine parts clean and reduce fuel consumption.

If acceptable water tolerance properties and pH levels are not maintained, lubricants will develop reduced power transmission properties and cause corrosion of the engine parts. Fluid flow is not smooth when water separates out and the separated water can be vaporized to steam at high temperature. These properties are particularly important in connection with functional fluid compositions.

Manufacturers of equipment requiring the use of functional fluids and lubricants often require that such fluids and lubricants process specific water tolerance and/or stability properties. For example, manufacturers of agricultural tractor machinery have specific requirements with respect to the water tolerance properties of tractor fluids used in connection with the machinery which the manufacturer believes to be necessary for the equipment to operate successfully under severe conditions. Low pH levels in an engine oil can greatly increase engine corrosion.

Fluids with poor water tolerance properties becomes turbid and the clarity of functional fluids often impacts greatly on the fluid's marketability. A fluid that is turbid or becomes turbid after a short period of use is often unacceptable to consumers regardless of the performance characteristics of the fluid. Improved clarity not only increases marketability but allows the user to more readily and accurately determine when the fluid should be replaced. A combination of poor water tolerance and low pH can be particularly damaging to performance.

U.S. Pat. No. 4,579,672 discloses functional fluids and lubricants having improved water tolerance properties. The compositions are comprised of major amounts of a synthetic or mineral oils of lubricating viscosity with minor amounts of oil soluble alkoxypolyethyleneoxy acid phosphite ester compounds dispersed therein as the water tolerance improving compounds.

U.S. Pat. No. 3,791,971 discloses polyoxyalkylene glycols and their reaction products with organic diisocyanate and dicarboxylic acid. These reaction products are combined with alkaline earth metal carbonates and dispersed in a hydrocarbon medium to provide lubricating compositions which are indicated as having superior acid neutralization capability and rust inhibiting properties when used within internal combustion engines. A number of compounds are disclosed throughout the 3,791,971 patent such as those encompassed by the general structural formulation shown at column 2, lines 44–55.

U.S. Pat. No. 4,265,774 discloses high molecular weight polygylcerol derivatives which are indicated as being useful as thickening agents for water-based lubricants. A large number of compounds encompassed by the general structural formula as shown at column 1, lines 35–45 are disclosed.

U.S. Pat. No. 3,625,893 discloses lubricating oil compositions which include minor amounts of basic group II metals salts of carboxylic acids and napthenic acids. The oil compositions including the additives are indicated as having improved oxidation stability and antirust properties.

U.S. Pat. No. 4,088,590 discloses brake fluids and operating fluids for central hydraulic installations in motor vehicles which are indicated as having excellent temperature/viscosity behavior as well as good lubricating properties. The improved properties are indicated as being obtained by including additives in the form of polyethylene glycol alkyl ether-based fluids of alkyl polyethylene glycol-t-butyl ethers. Amounts of the additive and a structural formula encompassing the additive is shown within the 4,088,590 patent at column 1, lines 7–19.

U.S. Pat. No. 3,856,688 discloses multi-purpose grease compositions which include thickening agents in the form of dibasic fatty acid soap compounds. The general structural formula of the dibasic fatty acid soap compounds utilized as the thickening agents is disclosed within the patent at column 1, line 60 with the variables defined thereafter.

U.S. Pat. No. 3,828,086 discloses dibasic fatty acid soap compounds which can be utilized as thickening agents. The general structural formula of the dibasic fatty acid soap compositions is disclosed in the patent at column 2, line 10 and defined thereafter.

U.S. Pat. No. 2,801,972 discloses stable lubricating greases which are prepared by incorporating into lubricating oils a grease thickener. The grease thickener is obtained by fusing high molecular weight ether derivatives having a primary alcohol group with an alkali, particularly caustic soda or pot ash. The general structural formula of the ether alcohols indicated as being useful in connection with the invention is given in the patent at column 2, line 45 and defined thereafter.

The U.S. parent application, serial number 07/020/287, filed February 27, 1987 upon which the present application is claiming priority was filed as a PCT application on Feb. 19, 1988 which application was published on Sept. 7, 1988 as W088/06615.

The present inventors have discovered that improved functional fluids and lubricating compositions such as crank case oils can be obtained by combining major amounts of an oil of lubricating viscosity with a minor amount of an additive component. In this limited respect, the present invention relates to the same general concept which is being carried out in the patents discussed above. However, the compounds which the present inventors utilize as the additive component is structurally different from and chemically distinct from the compounds referred to in the above-discussed patents. Although some of the compounds per se utilized by the present inventors to improve performance properties of compositions may not be completely novel compounds per se, such compounds as included within the oil compositions are novel compositions.

Sandoz Product Bulletin 7-200/85 refers to a number of surfactant compounds sold under the trademark Sandopan. These compounds generally conform to the formula:

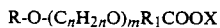

where R is a fatty group containing 13 to 18 carbons, n is 2 to 4, m is 1 to 100, $R_1$ is $CH_2$ to $C_3H_6$ and X is H or Na. These compounds are indicated as being useful in products such as cleaning fluids, cosmetics and toiletries.

SUMMARY OF THE INVENTION

The present invention is based on the discovery by the present inventors that certain performance properties of oil based lubricating compositions can be improved by including within the composition small amounts of an overbased salt of a compound represented by the general formula (I):

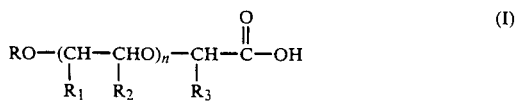

wherein R is a hydrocarbyl containing 1 to 44 carbons, $R_1$, $R_2$, and $R_3$ are independently hydrogen or an alkyl moiety containing 1 to 21 carbons, n is in the range of from 1 to 20.

A primary object of the present invention is to provide a lubricating composition comprised of an oil of lubricating viscosity having therein an additive which increases the performance characteristic of the composition.

Another object is to provide such a composition wherein the additive is in the form of an overbased salt of a compound of formula (I):

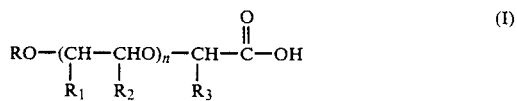

wherein R is a hydrocarbyl containing 1 to 44 carbons, $R_1$, $R_2$, and $R_3$ are independently hydrogen or an alkyl moiety containing 1 to 21 carbons, n is in the range of from 1 to 20.

An advantage of the present invention is the additive compound provides an improvement in more than one performance characteristic of the composition.

Another advantage of the present invention is that the additive compound provides improvement with respect to pH stability, water tolerance and frictional properties while not adversely affecting the anti-wear properties of the composition.

A feature of the present invention is that the additive compound reduces turbidity of fluids having contaminant water therein.

Another feature of the present invention is that the additive is effective in reducing wear and corrosion under extreme temperature and pressure conditions.

Another feature of this invention is that it provides improved water compatibility to functional fluids and lubricating compositions which are subjected to severe operational conditions.

Another advantage of this invention is that the additive compound can be included within an oil of lubricating viscosity in relatively small amounts at a relatively low cost.

Another feature of the present invention is that the functional fluids and lubricating compositions of the invention with the additive compound therein meet various agricultural machinery manufactures' specifications with respect to water tolerance properties.

Yet another feature of the present invention is that it provides a composition having a relatively high degree of clarity which can be maintained with contaminant water under severe operational conditions.

Another feature of the invention is that it aids in preventing water separation and thus aids in preventing water vaporization under high temperature conditions.

Another advantage of the invention is that it provides an additive which can be included in systems such as crank case oils and in particular diesel engine crank case oils contaminated with water in order to provide improved water tolerance properties, a stabilized pH and reduced turbidity.

Still another advantage of the present invention is that the additive compounds disclosed can be overbased.

Still another feature of the invention is that the overbased additive compounds of the invention provide a means of reducing the rate of acid build up in the system in which they are used with particularly good results being obtainable in connection with diesel engine crank case oils.

These and other objects, advantages and features of the present invention will become apparent to those persons skilled in the art upon reading the details of the structure synthesis and useage as more fully set forth below. Reference being made to the accompanying general structural formulae forming a part hereof wherein like symbols refer to like molecular moieties throughout.

DETAILED DESCRIPTION OF THE PREFERRED EMBODIMENTS OF THE INVENTION

Before the present oil based compositions containing the additive of the invention and processes for making such are described, it is to be understood that this invention is not limited to the particular compositions, additives or processes described as such may vary. It is also to be understood that the terminology used herein is for the purpose of describing particular embodiments only, and is not intended to be limiting since the scope of the present invention will be limited only by the appended claims.

The present inventors have determined that it is possible to greatly improve the water tolerance characteristics and pH stability of various compositions such as lubricating oils and functional fluids by including a particular additive compound therein. More specifically, the present inventors discovered that the water tolerance, pH stability, antiwear and other characteristics of a diesel engine crank case oil composition can be improved by including therein an additive in the form of overbased salts of iso-stearylpentaethyleneglycolacetic acid. Related compounds encompassed by the present invention are overbased salts of compounds represented by the general formula (I):

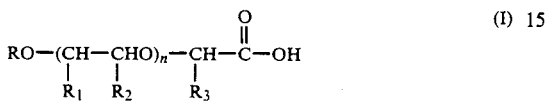

wherein R is a hydrocarbyl containing 1 to 44 carbons, $R_1$, $R_2$ and $R_3$ are independently hydrogen or an alkyl moiety containing 1 to 21 carbons, and n is in the range of from 1 to 20.

In that $R_1$, $R_2$ and $R_3$ are all preferably H, the preferred structural formula is represented by the general formula (II):

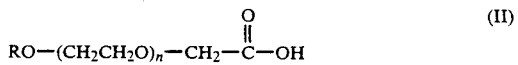

The substituent groups for the above formula (I) as well as formula (II) will now be described in greater detail in order to disclose and describe a representative number of examples of additive compounds of the invention and disclose preferred and particularly preferred embodiments.

In formula (I), and formula (II) and elsewhere in the disclosure hydrocarbyl means "hydrocarbon-based." As used herein, the term "hydrocarbon-based," "hydrocarbon-based substituent" and the like denotes a substituent having a carbon atom directly attached to the remainder of the molecule and having predominantly hydrocarbyl character within the context of this invention.

Examples of hydrocarbyl substituents which might be useful in connection with the present invention include the following:

(1) hydrocarbon substituents, that is, aliphatic (e.g., alkyl or alkenyl), alicyclic (e.g., cycloalkyl, cycloalkenyl) substituents, aromatic, alkphatic and alicyclic-substituted aromatic nuclei and the like as well as cyclic substituents wherein the ring is completed through another portion of the molecule (that is, for example, any two indicated substituents may together form an alicyclic radical);

(2) substituted hydrocarbon substituents, that is, those substituents containing nonhydrocarbon radicals which, in the context of this invention, do not alter the predominantly hydrocarbon substituent; those skilled in the art will be aware of such radicals (e.g., halo (especially chloro and fluoro), alkoxy, mercapto, alkylmercapto, nitro, nitroso, sulfoxy, etc.);

(3) hetero substituents, that is, substituents which will, while having predominantly hydrocarbyl character within the context of this invention, contain other than carbon present in a ring or chain otherwise composed of carbon atoms. Suitable heteroatoms will be apparent to those of ordinary skill in the art and include, for example, sulfur, oxygen, nitrogen and such substituents as, e.g., pyridyl, furanyl, thiophenyl, imidazolyl, etc., are exemplary of these hetero substituents.

In general, no more than about three radicals or heteroatoms and preferably no more than one, will be present for each ten carbon atoms in the hydrocarbon-based substituents. Typically, there will be no such radicals or heteroatoms in the hydrocarbon-based substituent and it will, therefore, by purely hydrocarbon.

Referring to formula (I) and formula (II) above, some specific examples of preferred R groups include the following:

(1) Alkylated aromatics like dodecylphenyl
(2) $C_{12-22}$ linear alkyl
(3) $C_{10-18}$ branched alkyl
(4) $C_{12}$-$C_{40}$ 2-alkyl,alkyl The above groups include the following R groups which are particularly preferred:

(1) iso-stearyl;
(2) $C_{24-28}$ alkylphenyl
(3) $C_{16-18}$ alkyl
(4) $C_{16-28}$ 2-alkyl, alkyl Additives of the present invention included in function fluids or lubricant oils will likely include a statistical mixture of compounds wherein different additive compounds vary, one from the other, in small increments, over a range. For example, a preferred statistical mixture of compounds might be present wherein the R group of either formula (I) or (II) is an alkyl moiety containing 16 to 18 carbon atoms such that the average number of carbons is about 17.

$R_1$, $R_2$ and $R_3$ are independently hydrogen or an alkyl moiety containing 1 to 21 carbons and each is preferably hydrogen. The overbased compounds of the invention must be oil soluble or oil dispersible and this property is effected by the length of R, and for formula (I) the length of $R_1$, $R_2$, and $R_3$ Accordingly, as the number of carbons in R should not be decreased below a certain point, unless formula (I) is utilized and the number of carbons in $R_1$, $R_2$ and/or $R_3$ is increased to provide for oil solubility of the compound (I).

It should be noted that although the overbased compound of the present invention must be oil soluble in the final composition it may not be soluble in oil by itself but have its solubility effected by other additives present in the fully formulated composition. Further, the overbased compounds of the present invention may be merely dispersible in a given concentrate but become dissolved as the proportional amount of oil is increased.

The overbased compounds of the inventions are preferably dispersable in oil either by themselves or in the presence of any other additive components and are more preferably readily soluble in oil either by themselves or in the presence of any other additive components normally present in crank case oils, specifically diesel engine crank case oils.

Some typical examples of $R_1$, $R_2$ and $R_3$ include H, $CH_3$, $C_2H_5$ and other straight and branched chain alkyl groups containing up to about 21 carbons. Preferably, one of $R_1$, $R_2$ or $R_3$ is hydrogen . At least one of $R_1$ or $R_2$ should be hydrogen. When $R_1$, $R_2$ and $R_3$ are not hydrogen a $CH_3$ moiety is preferred. In one preferred embodiment $R_1$ and $R_3$ are hydrogen and $R_2$ is methyl, it is particularly preferred if $R_1$, $R_2$, and $R_3$ are all hydrogen.

The variable n can range from 1 to about 20. Although n is an integer for any particular molecule, it should be pointed out that any given sample of an overbased compound of the present invention is likely to include a number of molecules of the compounds of the invention wherein n varies from one molecule to the next in increments over a range resulting in a statistical average for all the molecules. Accordingly, a sample may result wherein n is not a whole number, e.g., n is 4.5. Although n might be 1 to 20, it is preferably 1 to 6 and more preferably 4 to 6 for an average of 5 for obtaining improvement in water tolerance and antiwear properties in a functional fluid as well as improved detergent and frictional properties in a crank case oil. Stating that n is preferably 5 means that a preferred composition includes molecules of the overbased compounds of the invention which have a statistical average for their n values of about 5.

The variable X may be any cation and includes cations of H, Ca, Mg, Na, Zn, Ba, Li, K or NH diethyl amine and and triethyl amine. Preferred examples of X include cations of Ba, Na, Ca, Mg, and Zn. The inventors have found that X is most preferably a Ca or Mg cation.

Some specific examples of compounds of the present invention include overbased salts of iso-stearylpentaethyleneglycol-acetic acid; iso-stearyl-O-$(CH_2CH_2O)_5$-$CH_2CO_2Na$; lauryl-O-$(CH_2CH_2O)_{2.5}$ $CH_2CO_2H$; lauryl-O$(CH_2CH_2O)_{3.3}CH_2CO_2H$; oleyl-O-$(CH_2CH_2CHO)_4CH_2CO_2H$; lauryl-O-$(CH_2CH_2O)_{4.5}CH_2CO_2H$; lauryl-O-$(CH_2CH_2CHO)_{10}CH_2CO_2H$; lauryl-O$(CH_2CH_2O)_{16}CH_2CO_2H$; octylphenyl-O-$(CH_2CH_2O)_{-8}CH_2CO_2H$; octylphenyl-O$(CH_2CH_2O)_{19}CH_2CO_2H$; 2-octyldecanyl-O-$(CH_2CH_2O)_6CH_2CO_2H$.

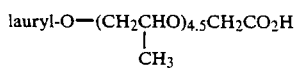

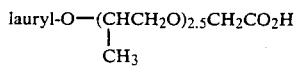

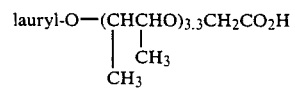

The terms "overbased salt," "overbased salt complex" and "basic salt" are used to designate salts wherein the cation portion such as the metal cation is present in stoichiometrically larger amounts than the organic acid radical. The commonly employed methods for preparing the basic salts such as overbased metal salts involve heating a mineral oil solution of an acid with a stoichiometric excess of a metal neutralizing agent such as the metal oxide, hydroxide, carbonate, bicarbonate, or sulfide at a temperature above 30° C. and filtering the resulting mass. The use of a "promoter" in the neutralization step to aid the incorporation of a large excess of metal likewise is known. Examples of compounds useful as the promoter include phenolic substances such as phenol, naphthol, alkylphenols, thiophenol, sulfurized alkylphenols, and condensation products of formaldehyde with phenolic substances; alcohols such as methanol, 2-propanol, octyl alcohol, Cellosolve, Carbitol, ethylene glycol, stearyl alcohol and cyclohexyl alcohol; and amines such as aniline, phenylenediamine, phenothiazine, phenyl-beta-naphthylamine and dodecylamine.

A particularly effective method for preparing the basic salts comprises mixing an acid with an excess of a basic alkaline earth metal neutralizing agent and at least one alcohol promoter, (preferably methanol mixed with other alcohols like hexanol and amyl alcohols) and carbonating the mixture at an elevated temperature such as 30° to 200° C. Overbased complexes are disclosed in U.S. Pat. No. 3,714,042 which is incorporated herein by reference to disclose such complexes and their method of preparation.

Compositions of the present invention may be sold in concentrates in a diluent oil, in combination with any other known additive which includes, but is not limited to, dispersants, detergents, antioxidants, antiwear agents, extreme pressure agents, emulsifiers, demulsifiers, friction modifiers, anti-rust agents, corrosion inhibitors, viscosity improvers, dyes, and solvents to improve handleability which may include alkyl and/or aryl hydrocarbons. These additives may be present in various amounts depending on the needs of the final product. The compositions of the present invention have been found to be particularly useful as additive components in crank case oils and more particularly in diesel engine crank case oils.

The concentrate might containing 50% to 90% by weight of one or more overbased salt compounds of the present invention. Overbased salt compounds of the invention may be present in a final product in an amount in the range of from about 0.01% to about 20% by weight based on the weight of the final fully formulated composition. As pointed out above overbased salts of the compound of formula (I) and (II) are not generally present in a single molecular form but rather as a statistical mixture of molecules varying each from the other slightly over a range. Such statistical mixtures are easier to produce than a pure form of any given single molecule and are believed to provide for improved performance, particularly in crank case oil formulations.

The following examples are provided so as to provide those of ordinary skill in the art with a complete disclosure and description how to make compounds and compositions of the invention. These examples are not intended to limit the scope of what the inventors regard as their invention. Efforts have been made to insure accuracy with respect to numbers used (e.g. amounts, temperature, etc.) but some experimental errors and deviation should be accounted for. Unless indicated otherwise, parts are parts by weight, temperature is in degrees C., and pressure is at or near atmospheric. It should also be noted that all examples result in compounds which can be overbased or overbased to a greater degree by the addition of a metal hydroxide such as $Ca(OH)_2$ combined with $CO_2$ bubbling. The amount of $Ca(OH)_2$ added will effect the amount of overbasing obtained when the $Ca(OH)_2$ is followed by $CO_2$ bubbling in appropriate amounts. The $CO_2$ bubbling is generally done at a rate of one standard cubic foot per hour (SCF/h) but can be done at different rates. The relative amounts of $Ca(OH)_2$ and $CO_2$ bubbling can be calculated by those skilled in the art.

EXAMPLE A

Charge a flask with 210 grams of isostearyl pentaethylene glycol acetic acid, 20 grams of ZnO and 100 grams of toluene. Heat the mixture to 110° C. Continue heating in order to take off about 15 ml of azeotroped water and allow to cool. Remove the solvent by means of a Barrett receiver trap and heat the mixture to 160° C. for 4 hours. Cool the mixture to 120° C. and filter the reaction mixture over DD1600 until clear and wash the pad with toluene. Concentrate the filtrate under vacuum and collect the residue in the form of a zinc salt of the starting acid.

EXAMPLE B

Charge a flask with a mixture of Na salts of compounds encompassed by general structural formula (I) wherein n is 5, $R_1$, $R_2$ and $R_3$ are hydrogen and R contains 16–18 carbon atoms and may be branched or straight. Combine the mixture of compounds of structural formula (I) in an amount of 793 grams with 300 ml of toluene and heat the mixture in order to azeotrope off about 50 ml of water. Allow the mixture to cool to 80° C. and add 89.4 grams of $CaCl_2$ dissolved in 80 grams of water. Heat the mixture at 100° C. in order to azeotrope off about 80 ml of water and add additional toluene to the reacting mixture. Filtering can be carried out as indicated in Example A above in order to collect a calcium salt filtrate.

EXAMPLE C

Charge a flask with a compound encompassed by general structural formula (II) wherein n is 5 and R is alkyl and varies over a range of 16–18 carbons. The compound of structural formula (II) should be added in an amount 250 grams to a flask along with 86 grams of $Ca(OH)_2$ and 25 grams of a polyisobutylene substituted maleic anhydride, 120 grams of methanol, 248 grams of diluent oil and a 1000 grams of toluene. The mixture is to be heated in a flask to 45° C. and carbon dioxide gas is bubbled through the mixture. Add 86 grams of $Ca(OH)_2$ and continue the bubbling of the carbon dioxide until a strong base number (in the range of 10–50) is obtained. Heat the mixture to 150° C. in order to remove water and remove water and methanol via a Barrett receiver trap. Centrifuge the mixture and decant off organic material. Add 26 grams of the polyisobutenyl substituted maleic anhydride and concentrate the mixture by heating to 110° C. at 30–40 mmHg.

EXAMPLE D

Charge a flask with a statistical mixture of compounds encompassed by general structural formula (I) wherein $R_1$, and $R_3$ are hydrogen, $R_2$ is methyl, n varies over a range to provide an average of about 5 and R is propyl. The mixture of compounds of structural formula (I) should be added in an amount 250 parts to a flask along with 50 parts of $Ca(OH)_2$ and 100 parts of methanol, 200 parts of diluent oil and 1000 parts of toluene. Heat the mixture in a flask to about 45° C. and bubble carbon dioxide gas through the mixture for about 30 minutes. Additional 50 part incremental amounts of $Ca(OH)_2$ are added and carbon dioxide bubbling is carried out with the addition of each incremental amount of $Ca(OH)_2$. When the desired amount of overbasing has been obtained by the addition of incremental amounts of $Ca(OH)_2$, heat the mixture to 150° C. in order to remove water and methanol via a Barrett receiver trap. Centrifuge the mixture and decant off organic material.

EXAMPLE E

Charge a flask with a compound encompassed by general structural formula (II) wherein n is 5 and R is aromatic. The compound of structural formula (II) should be added in an amount 100 parts to a flask along with 25 parts of $Ca(OH)_2$ and 50 parts of an alcohol promoter which is 50% methanol, 25% hexanol and 25% amyl alcohols, 100 parts of diluent oil and 400 parts of toluene. Heat the mixture in a flask to 45° C. and bubble carbon dioxide gas through the mixture at a sufficient rate and for sufficient time based on the amount of $Ca(OH)_2$ added. Add additional incremental amounts of $Ca(OH)_2$ (25 parts each) with heat and $CO_2$ bubbling with each addition until the desired base number is obtained. A high degree of overbasing can be obtained by this method. Heat to 150° C. with $N_2$ bubbling in order to remove water and alcohols. Filter to obtain product.

EXAMPLE F

Charge a flask with a mixture of Na salts of compounds encompassed by general structural formula (II) wherein n varies over a range of from 4 to 6 and R is an alkyl substituted aromatic. The compounds of structural formula (II) should be added in an amount of 100 parts to a flask along 50 parts of calcium chloride. Then add 25 parts of $Ca(OH)_2$ and 50 parts of an alcohol promoter which is 50% methanol, 25% hexanol and 25% amyl alcohols, 100 parts of diluent oil and 400 parts of toluene. Heat the mixture in a flask to 45° C. and bubble carbon dioxide gas through the mixture at a sufficient rate and time to react with the calcium ions and form an overbased calcium complex. Add additional incremental amounts of $Ca(OH)_2$ (25 parts each) with heat and $CO_2$ bubbling with each addition until the desired base number is obtained. A high degree of overbasing can be obtained by this method. Heat to 150° C. with $N_2$ bubbling in order to remove water and alcohols. Filter to obtain product.

EXAMPLE G

Charge a flask with a compound encompassed by general structural formula (I) wherein $R_1$ is hydrogen and $R_2$ and $R_3$ are methyl, n provides a statistical average of 5 and R is isostearyl. The compound of structural formula (I) should be added in an amount 100 parts to a flask along with 25 parts of $Ca(OH)_2$ and 100 parts of an alcohol promoter which is 40% methanol, 20% hexanol and 40% amyl alcohols, 100 parts of diluent oil and 400 parts of toluene. Heat the mixture in a flask to 45° C. and bubble carbon dioxide gas through the mixture until the desired Ca salt complex has been formed. Add additional incremental amounts of $Ca(OH)_2$ (25 parts each) with heat and $CO_2$ bubbling with each addition until the desired base number is obtained. A high degree of overbasing can be obtained by this method. Heat to 150° C. with $N_2$ bubbling in order to remove water and alcohols. Filter to obtain product.

EXAMPLE 1

A concentrate containing the multi-functional additive component of the present invention can be prepared by adding the salt prepared in accordance with Example C above to 100 grams of a diluent oil. The diluent oil can be added to functional fluids in order to improve characteristics of the fluid. Specifically, the addition of 0.5 to 2.5% by weight of the salt prepared in Example C can be added to a functional fluid in order to improve the water tolerance of the fluid without adversely affecting anti-wear and extreme pressure characteristics.

EXAMPLES 2-6

In order to prepare examples 2, 3, 4, 5 and 6, add 1% to 2% by weight of the salts and/or mixed salts prepared in accordance with Examples A, B, C, D and E respectively to a suitable diluent oil of lubricating viscosity.

EXAMPLE 7

Prepare a salt of the acid encompassed by general structural formula (I) using the procedure of Example B above while including some components of structural formula (I) wherein R is an aromatic moiety and n ranges from 4–6. Add the salt obtained to diluent oil in sufficient amounts so that the salt becomes dissolved in the diluent oil to the extent that the oil is not cloudy. This concentrate can be added to a functional fluid such as a tractor fluid in order to improve water tolerance characteristics of the tractor fluid. The concentrate should be added so that the salt present in the concentrate is ultimately present within the functional fluid in an amount of about 0.5% to about 2.5% based on the weight of the fluid.

EXAMPLES 8-14

Prepare examples 8, 9, 10, 11, 12, 13 and 14 respectively, by adding 0.1 parts to 20 parts of the salt and/or mixed salt of examples A, B, C, D, E, F, G to a suitable oil of lubricating viscosity. The amount of salt of Examples A–G to be added varies depending on the end need requirements of the lubricant.

It should be noted that each of the salts described above in Examples A–G can be converted to concentrates by adding these salts to diluent oils. Further, these concentrates can be formed into additive package concentrates by combining the salt and diluent oil with any combination of know additives such as dispersants, detergents, antioxidants, antiwear-agents, extreme pressure agents, emulsifiers, demulsifiers, friction modifiers, anti-rust agents, corrosion inhibitors, viscosity improvers, dyes, solvents and other known additive components. These concentrates and/or concentrate packages can be added to functional fluids such as hydraulic fluids and/or tractor fluids in order to improve characteristics of the fluids such as to improve the water tolerance properties of the functional fluid.

FORMULATED ADDITIVE PACKAGES AND FULLY FORMULATED OIL COMPOSITIONS

As indicated above, the salts of the present invention as well as the salts in the form of concentrates in diluent oils can be combined with a number of other different additives to provide fully formulated packages and fully formulated oil compositions. It has been found that the overbased salt compounds of the present invention have particularly good results when utilized within fully formulated crank case oil package concentrates which can be used in the production of fully formulated crank case oil compositions and more specifically fully formulated diesel oil crank case compositions. The diesel oil compositions of the present invention include about 2 to 6 weight percent of the overbased salt compositions of the present invention. The overbased salt compositions of the present invention have excellent detergent properties in crank case motor oil formulations. When the overbased compositions of the present invention were utilized within diesel crank case oils, the oils passed the Cat 1G2 Engine Test providing excellent overall engine cleanliness as compared with similar packages which contained a well known commercial detergent in the form of calcium salicylate.

Fully formulated crank case oils may include the overbased salt compounds of the present invention in combination with:

1. VI improvers in an amount in the range of about 0.3 to 2 weight percent chem (i.e. chemical without any diluent oil) which VI improvers are generally in the form of hydrogenated butadiene/styrene copolymers which can be purchased from BASF under the tradename Glissoviscol SG.

2. Antiwear agents in an amount in the range of about 0.5% to 3 weight percent which antiwear agents are generally in the form of zinc dithiophosphate compounds. Such zinc dithiophosphate anti-wear agents may be formed by reacting phosphorus pentasulfide with a mixture of alcohols such as isopropyl and methyl amyl alcohols and then neutralizing the acidic product with a zinc oxide. The amount of total phosphorus should be kept below acceptable regulatory levels if applicable.

3. Nitrogen-containing and/or polyol dispersants may be added in a total amount of about 1 to 15 weight percent. Such dispersants are generally in the form of condensation products obtained from the reaction between a polyamine and/or polyol and a high molecular weight alkylated succan. The alkylated succan is derived from reacting an unsaturated polyisobutene polymer having a molecular weight of about 1,000 to 3,000 with a maleic anhydride. The polyamines and/or polyols are then reacted with the alkylated succan. The polyamines are residual by-products left from the distillation of products from the reaction between ammonia and 1, 2-dichlorylethane.

4. Additional detergent in an amount of about 0.2 to 3 weight percent can be added with the detergent being a highly overbased form of calcium or magnesium salicylate having a conversion of about 600. Such detergents can be purchased from Shell Oil Company under the tradename Sap 007 or alternatively under the tradename AC-60 which is a calcium overbased salicylate detergent having a conversion of about 250. Phenate detergents may be added as complete or partial replacements for the salicylate detergents. The phenate detergents may be ashless or nitrogen containing detergents and/or overbased or magnesium containing detergents. Such phenates may also be added in addition to the salicylate compounds in amounts of about 0.2 to 4 weight percent.

5. An additional detergent in the form of a highly overbased calcium and/or magnesium and/or sodium sulfonate detergent can also be added in amount of about 0.2 to 3 weight percent. Such detergents are sulfonates having a molecular weight of about 430 and a conversion of approximately 1,000.

6. Small amounts of anti-foaming agents may also be added to the formulation. Such anti-foaming agents are generally present in an amount of about 50 to 200 parts per million. Such anti-foaming agents are well known commercial products known and available to those skilled in the art.

7. Small amounts of other known additives may also be present such as pour point depressants 0.1 to 0.3 weight percent and antioxidants.

GENERAL FORMULATED EXAMPLE I

Prepare a fully formulated crank case oil by starting with a 15W-40 weight oil as the base oil and adding thereto about 0.3 to 2 weight percent of a VI improver; 0.1 to 0.3 weight percent of a pour point depressant; 0.5 to 5 weight percent of an overbased composition of the present invention in the form of an overbased calcium carboxylate of a mixture of compounds of formula (II) wherein n averages about 5 and R is a hydrocarbon containing 16 to 18 carbons (conversion in the range of 110 to 1500); 0.5 to 3 weight percent of anti-wear agent in the form of zinc dithiophosphates; 1 to 15 weight percent of a basic nitrogen containing dispersant in the form of a condensation product formed by reacting a polyamine and a high molecular weight alkylated succan; 0.2 to 3 weight percent of an overbased magnesium salicylate (having a conversion of about 600); 0.2 to 3 weight percent of a detergent in the form of an overbased calcium sulfonate (having a conversion of about 1200); 50 to 200 ppm of an anti-foaming agent.

FULLY FORMULATED EXAMPLE II

Prepare a fully formulated diesel engine crank case oil by starting with a 15W-40 weight oil as the base oil and adding thereto 1.4 weight percent of a VI improver in the form of a hydrogenated butadiene/styrene copolymer; 0.3 weight percent of a pour point depressant in the form of a polymethacrylate polymer; 3.27 weight percent of an overbased composition of the present invention in the form of an overbased calcium carboxylate of a mixture of compounds of formula (II) wherein n is an average of about 5 and R is a hydrocarbon containing 16 to 18 carbons (conversion in the range of 175 to 200); 0.59 weight percent of a diluent oil with 1.15 weight percent of anti-wear agent in the form of zinc dithiophosphates; 5.5 weight percent of a basic nitrogen containing dispersant in the form of a condensation product formed by reacting a polyamine and a high molecular weight alkylated succan; 1.5 weight percent of an overbased magnesium salicylate (having a conversion of about 600); 1.49 weight percent of a detergent in the form of an overbased calcium sulfonate (having a conversion of about 1,200); 110 ppm of an anti-foaming agent.

FULLY FORMULATED EXAMPLE III

Prepare a fully formulated crank case oil by starting with a 10W-40 weight oil as the base oil and adding thereto about 1.5 weight percent of a VI improver in the form of a hydrogenated butadiene/styrene copolymer; about 0.25 weight percent of a pour point depressant in the form of a polymethacrylate polymer; about 3 weight percent of an overbased composition of the present invention in the form of an overbased calcium carboxylate of a mixture of compounds of formula (II) wherein n averages about 5 and R is a hydrocarbon containing 16 to 18 carbons (conversion in the range of 175 to 200); about 1.0 weight percent of anti-wear agent in the form of zinc dithiophosphates; about 5 weight percent of a basic nitrogen containing dispersant in the form of a condensation product formed by reacting a polyamine and a high molecular weight alkylated succan; about 1.5 weight percent of an overbased magnesium salicylate (having a conversion of about 600); about 1.5 weight percent of a detergent in the form of an overbased calcium sulfonate (having a conversion of about 1200); about 100 ppm of an anti-foaming agent.

FULLY FORMULATED EXAMPLE IV

Prepare a fully formulated diesel engine crank case oil by starting with a 15W-40 weight oil as the base oil and adding thereto 1 weight percent of a VI improver in the form of a hydrogenated butadiene/styrene copolymer; 0.2 weight percent of a pour point depressant in the form of a polymethacrylate polymer; 3 weight percent of an overbased composition of the present invention in the form of an overbased calcium carboxylate of a mixture of compounds of formula (II) wherein n is an average of about in the range of 1 to 6 and R is a hydrocarbon containing 16 to 18 carbons (conversion in the range of 110 to 1,400); 2 weight percent of anti-wear agent in the form of zinc dithiophosphates; 5 weight percent of a dispersant formed by reacting a polyol and a high molecular weight alkylated succan; 1.5 weight percent of a detergent in the form of an ashless phenate and 1.6 weight percent of a detergent in the form of a magnesium phenate; 1.5 weight percent of a detergent in the form of an overbased calcium sulfonate (having a conversion of about 1,200); 100 ppm of an anti-foaming agent.

FULLY FORMULATED EXAMPLE V

Prepare a fully formulated crank case oil by starting with a 10W-40 weight oil as the base oil and adding thereto about 1.5 weight percent of a VI improver in the form of a high molecular weight copolymer; about 0.3 weight percent of a pour point depressant in the form of a polymethacrylate polymer; about 5 weight percent of an overbased composition of the present invention in the form of an overbased mixed salts of magnesium and calcium carboxylates wherein the mixture of salt compounds of formula (II) are present wherein n averages about 5 and R is a hydrocarbon containing 14 to 22 carbons (conversion in the range of 175 to 200); about 1.0 weight percent of anti-wear agent in the form of zinc dithiophosphates; about 5 weight percent of a basic nitrogen containing dispersant in the form of a condensation product formed by reacting a polyamine and a high molecular weight alkylated succan; about 0.5 weight percent of an overbased magnesium salicylate (having a conversion of about 600); about 1.5 percent of an ashless phenate and 1.5 weight percent of an overbased magnesium phenate; about 1.5 weight percent of a detergent in the form of an overbased calcium sulfonate (having a conversion of about 1200); about 100 ppm of an anti-foaming agent.

The present invention has been disclosed and described herein in what is believed to be its preferred embodiments. However, modifications will occur to those skilled in the art upon reading this disclosure and such modifications are intended to be encompassed by the present invention.

What is claimed is:

1. A crank case oil composition, comprising:
    an oil of lubricating viscosity in an amount of 50% or more by weight based on the total weight of the composition and a minor amount, sufficient to improve performance characteristics of the composition of oil dispersible additive, comprising:
    an overbased salt of a compound having structural formula (I)

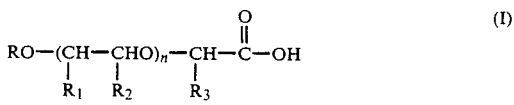

(I)

wherein R is a hydrocarbyl containing 1 to 44 carbons, $R_1$, $R_2$, and $R_3$ are independently hydrogen or an alkyl moiety containing 1 to 21 carbons, and n is in the range of from 1 to 20.

2. The crank case oil composition of claim 1 wherein the overbased salt is an oil soluble metal salt complex of the compound of formula (I) wherein R contains 12 to 24 carbons and $R_1$ and $R_3$ are hydrogen.

3. The crank case oil composition of claim 2 wherein n is in the range of 1 to 6 and the compound of formula (I) forms a salt with a cation selected from a group consisting of cations of Ca, Mg, Na, Zn, Ba, Li, K, $NH_4$, diethyl amine and triethyl amine.

4. The crank case oil composition of claim 3 wherein n is in the range of 4 to 6, $R_2$ is hydrogen and the cation is selected from a group consisting of Ca, Na, Mg and Zn.

5. The crank case oil composition of claim 1 wherein $R_1$ and $R_3$ are hydrogen and $R_2$ is methyl and the metal salt complex is an overbased calcium salt complex.

6. The crank case oil composition of claim 2 wherein the crank case oil is a diesel engine crank case oil, the metal salt complex is a calcium salt complex present in the form of a mixture of salts wherein n is an average of about 5, the mixture having a base number in the range of from about 50 to about 400 TBN and wherein the mixture of compounds of formula (I) is present in an amount in the range of from about 0.1 to about 20% by weight based on the weight of the crank case oil composition.

7. The crank case oil composition of claim 1, further comprising:
a VI improver in an amount of about 0.3 to 2 weight percent;
an anti-wear agent in an amount of about 0.5 to 3 weight percent; and
a nitrogen-containing dispersant in an amount of about 1 to 15 weight percent.

8. The crank case oil composition of claim 7, further comprising:
a detergent in an amount of about 0.2 to 7 weight percent in the form of magnesium salicylate and an overbased calcium sulfonate; and
an anti-foaming agent in an amount of about 50 to 200 parts per million.

9. An oil based composition, comprising:
a base oil of lubricating viscosity having therein 0.5% to 5% by weight of an overbased metal salt complex based on the total weight of the oil based composition, the metal salt complex being that which is formed by metal cations in the presence of a compound represented by the formula (II)

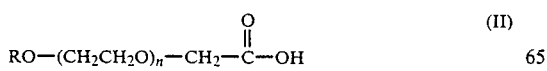

(II)

wherein n varies over a range to provide an average of about 5 and R is an alkyl containing 16 to 24 carbons.

10. The oil based composition of claim 9 wherein the metal salt complex is present in an amount in the range of 0.5% to about 3% by weight and the metal cations are Ca cations.

11. The oil based composition of claim 9 wherein the composition is a diesel engine crank case oil, the metal salt complex is present in an amount in the range of 0.5% to about 2.0% by weight, the metal cations are Ca and the overbased salt complex has a base number in the range of about 50 to 400 TBN.

12. An oil additive concentrate, comprising:
about 10% to about 50% by weight of an oil of lubricating viscosity; and
an overbased salt of a compound having structural formula (I):

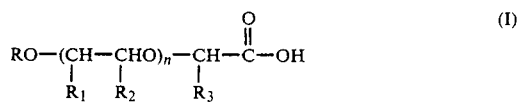

(I)

wherein R is a hydrocarbyl containing 1 to 44 carbons, $R_1$ and $R_3$ are hydrogen and $R_2$ is hydrogen or methyl, and n is an integer in the range of from 1 to 20.

13. The oil additive concentrate of claim 12 containing a mixture of overbased salts of the compound of formula (I) where R is a hydrocarbon and contains from 16 to 22 carbons and n averages about 5 and further wherein the compound of formula (I) is an oil soluble metal salt complex having a TBN in the range of from about 50 to about 400.

14. The oil additive concentrate of claim 12 wherein the compound of formula (I) is an overbased mixed salt complex.

15. The oil additive concentrate of claim 13 wherein the metal is Ca.

16. The oil additive concentrate of claim 12 wherein the compound of formula (I) is iso-stearylpentaethylene- ene-glycol-acetic acid and is present in the oil in an amount in the range of from about 60% to about 90% by weight based on the total weight of the concentrate.

17. The oil additive concentrate of claim 12 further comprising:
a VI improver in the form of hydrogenated butadiene/styrene copolymers;
an anti-wear agent in the form of zinc dithiophosphate compounds; and
a dispersant including a high molecular weight alkylated succan.

18. The oil additive concentrate of claim 17, further comprising:
a detergent in the form of an overbased magnesium salicylate and an overbased calcium sulfonate; and
an anti-foaming agent.

19. The oil additive concentrate as claimed in claim 17 wherein the dispersant is formed by reacting the high molecular weight succan with a compound selected from the group consisting of a polyamine and a polyol.

20. The oil additive concentrate as claimed in claim 17, further comprising:
an additional detergent selected from the group consisting of an ashless phenate and an overbased phenate.

* * * * *